United States Patent [19]

Arraudeau et al.

[11] Patent Number: 5,154,916
[45] Date of Patent: Oct. 13, 1992

[54] EYELASH MAKE-UP COMPOSITION BASED ON WAX AND KERATIN HYDROLYSATE

[75] Inventors: Jean-Pierre Arraudeau; Jeanne Patraud, both of Paris; Didier Gagnebien, Levallois-Perret, all of France

[73] Assignee: L'Oreal, Paris, France

[21] Appl. No.: 515,709

[22] Filed: Apr. 27, 1990

Related U.S. Application Data

[63] Continuation of Ser. No. 178,701, Apr. 7, 1988, abandoned.

[51] Int. Cl.⁵ ............................................. A61K 7/021
[52] U.S. Cl. ...................................... 424/63; 514/21; 514/844; 514/937; 424/401

[58] Field of Search ...................... 514/2, 21, 801, 844; 424/63, 401

[56] References Cited

U.S. PATENT DOCUMENTS 4,517,175  5/1985  Iwabuchi et al. ................... 514/801

FOREIGN PATENT DOCUMENTS 2167301  5/1986  United Kingdom ................ 514/844

*Primary Examiner*—David M. Naff
*Assistant Examiner*—Jean C. Witz
*Attorney, Agent, or Firm*—Cushman, Darby & Cushman

[57]  ABSTRACT

The wax-based mascaras containing keratin hydrolysates having a molecular weight greater than 50,000 have improved properties for coating eyelashes, of stability and eyelash lengthening.

19 Claims, No Drawings

EYELASH MAKE-UP COMPOSITION BASED ON WAX AND KERATIN HYDROLYSATE

This is a continuation of application Ser. No. 07/178,701, filed Apr. 7, 1988, now abandoned.

The present invention relates to a composition for eyelash make-up, generally called mascara.

To obtain a satisfactory eyelash make-up, the mascaras must have a certain number of characteristics: they must provide a homogeneous coating of the eyelashes which is stable over time, they must provide lengthening of the eyelashes and enable rapid application.

The mascaras used are generally wax-based. However, it has been observed that when waxes alone are used, a non-homogeneous film is obtained after application on the eyelashes which forms cracking flakes immediately after drying. To overcome this disadvantage, it has been proposed to add various additives to the wax. By the addition of a thickening agent, such as hydroxyethylcellulose, the homogeneity of the film deposited on the eyelashes is improved. However, the stability of this film is not sufficient because cracking flakes appear after a few hours. Moreover, the lengthening of the eyelashes is inadequate.

It has also been proposed to add to the mixture of wax and thickening agent a cohesion agent, such as colophony and its derivatives.

Mascaras are also known which are based on mixtures of waxes and anionic and cationic polymers.

These mascaras provide perfect coating of the eyelash and substantially increase the lengthening of the eyelash. Unfortunately, these cosmetics require a certain time for application in order to obtain the perfect coating of the eyelashes.

U.S. patent application Ser. No. 799,496 describes mascaras containing waxes and derivatives of sulfonated keratin having the formula:

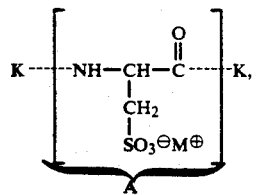

(I)

wherein:
K represents the keratin residue;
M⊕ represents H⊕, a cation derived from an alkaline metal or magnesium, or indeed N⊕(R)₄, wherein the R radicals are identical or different and represent a hydrogen atom or even an alkyl or hydroxyalkyl radical having at most 4 carbon atoms, with the symbol A representing from 3 to 15% by weight of the keratinic derivative.

The mascaras obtained provide very rapid application, substantial lengthening of the eyelashes and good stability.

In the present application, it has been found that by using another keratin derivative, a hydrolyzed keratin, excellent results were also obtained. The hydrolyzed keratin has the advantage of being used in much smaller quantities. In the following description, "keratin hydrolysate" will mean a partially hydrolyzed keratin.

The object of the present invention, therefore, is a composition for eyelash make-up, or mascara, comprising, in a cosmetically acceptable support, at least one wax having a melting point of between 60° and 110° C., characterized by the fact that it contains at least one keratin hydrolysate having an average molecular weight of between 50,000 and 200,000, with the weight ratio of the quantity of keratin hydrolysate used to the quantity of wax(es) used being between 0.005 and 0.5.

Hydrolysates having a molecular weight of approximately 100,000 are particularly suitable.

When the molecular weight is less than 50,000, the mascara does not provide satisfactory coating of the eyelashes. The filmogenic properties of the mascara are not satisfactory.

The keratin from which the keratin hydrolysate is prepared can come from hair, wool, hooves, horn, fur, silks or feathers.

Preferably, the keratin from skin is used since it is richer in sulfur compounds.

Preferably, the keratin hydrolysates used are those obtained by moderate alkaline hydrolysis.

In the alkaline hydrolysis method, the keratinic substance (hair, fur, hooves, etc.) is treated with a base mineral, such as sodium, potassium, barium hydroxide, lithium hydroxide, sodium carbonate, potassium carbonate or lithium carbonate, sodium silicate or borax. The hydrolysis reaction is monitored so as to have a product with a molecular weight which is greater than 50,000.

The keratin hydrolysate gives good results in a relatively low amount, between 0.05 and 5% by weight in relation to the total weight of the composition.

In general, the waxes selected have a melting point of between 60° and 110° C. and a needle penetration, at 25° C., of 3 to 40, as measured in accordance with U.S. Standard ASTM D5 or in accordance with French Standard NFT 004. The principle of the measurement of the penetration of a needle in accordance with Standards ASTM D5 and NFT 004 consists of measuring the depth, expressed in tenths of millimeters to which a standardized needle (weighing 2.5 g placed in a needle-holder weighing 47.5 g, or a total of 50 g) penetrates when placed on the wax for 5 seconds.

The waxes used in accordance with the invention are selected from among the animal waxes, the vegetable waxes, the mineral waxes, the synthetic waxes and the various fractions of natural waxes, with all such waxes having the two characteristics indicated above.

Among the animal waxes, beeswaxes, lanolin waxes and China insect waxes can be mentioned.

Among the vegetable waxes, Carnauba waxes, Candelilla waxes, Ouricurry waxes, cork fiber waxes, sugar cane waxes and Japan waxes can be mentioned.

For the mineral waxes, paraffins, microcrystalline waxes, Nontan waxes and ozocerites in particular can be mentioned.

For the synthetic waxes, polyethylene waxes, the waxes obtained by the Fisher and Tropsch synthesis and the waxy copolymers as well as their esters can in particular be mentioned.

These waxes are well known in the art. In accordance with the invention the wax(es) is (are) present in the mascara compositions in amounts of between 2 and 40% by weight in relation to the total weight of the composition.

The waxes which can be used in accordance with the present invention are preferably solid and rigid at a temperature of less than 50° C.

The mascara compositions in accordance with the present invention can contain pigments in addition to the keratin hydrolysate and the waxes. Due to the presence of the above-identified keratin hydrolysates, good distribution of said pigments in the compositions is obtained as is an improvement in their fixing on the eyelashes.

The pigments which can be used in accordance with the invention are selected from among the mineral pigments, the organic pigments and the pearly pigments.

By way of example of mineral pigments, titanium dioxide (rutile or annatase) possibly surface treated and codified in the Color Index under the reference CI 77 891, black, yellow, red and brown iron oxides, codified under the references CI 77 499, 77 492, 77 491, manganese violet (CI 77 742), ultramarine blue (CI 77 007), chromium oxide (CI 77 288), chromium hydrate (CI 77 289) and ferric blue (CI 77 510) can be mentioned.

The organic pigments are selected, in particular, from among the D and C red No. 19 (CI 45 170), D and C red No. 9 (CI 15 575), D and C red No. 21 (CI 45 380), D and C orange No. 4 (CI 15 512), D and C orange No. 5 (CI 45 370), D and C red No. 27 (CI 45 410), D and C red No. 13 (CI 15 630), D and C red No. 7 (CI 15 850), D and C red No. 6 (CI 15 850), D and C yellow No. 5 (CI 19 140), D and C red No. 36 (CI 12 085), D and C orange No. 10 (CI 45 425), D and C yellow No. 6 (CI 15 985), D and C red No. 30 (CI 73 360), D and C red No. 3 (CI 45 430) pigments and lacquers based on cochineal carmine (CI 75 470).

The pearly pigments can be selected from among the white pearly pigments such as mica covered with titanium oxide, bismuth oxychloride, the colored pearly pigments such as titanium mica with iron oxides, titanium mica with ferric blue, chromium oxide, etc., titanium mica with an organic pigment of the above-identified type as well as those based on bismuth oxychloride.

When the pigments are used, they are present in amounts of 3 to 20% by weight in relation to the total weight of the composition depending on the coloration and the intensity of the coloration which it is sought to obtain.

The composition in accordance with the present invention can in particular be in the form of oil-in-water or water-in-oil emulsions, or in the form of suspensions in a solvent medium, or even in an anhydrous solid or paste. The methods for the preparation of these various types of compositions are well known to the skilled artisan.

When they are used in the form of emulsions, the compositions can contain tensio-active agents which are well known in the art.

A particularly preferred embodiment consists of preparing anionic or non-ionic emulsions using anionic or non-ionic tensio-active agents in amounts preferably between 2 and 30% by weight in relation to the total weight of the composition.

Among the anionic tensio-active agents which can be used alone or in combination, the following can in particular be mentioned: the alkaline salts, the ammonium salts, the amine salts or the aminoalcohol salts of the following compounds:

alkylsufates, alkylether sulfates, alkylamide sulfates and ether sulfates, alkylarylpolyethersulfates, monoglyceride sulfates, alkylsulfonates, alkyl amide sulfonates, alkylarylsulfonates, α-olefin sulfonates, paraffin sulfonates, alkylsulfosuccinates, alkylethersulfosuccinates, alkylamide sulfosuccinates, alkylsulfosuccinamates, alkylsulfoacetates, alkylpolyglycerol carboxylates, aklylphosphates/alkyletherphosphates, aklylsarcosinates, alkylpolypeptidates, alkylamidopolypeptidates, alkylisothionates, alkyltaurates.

The alkyl radical in all these compounds generally designates a chain of 12 to 18 carbon atoms.

Other anionic tensio-active agents are composed of fatty acid salts such as oleic, ricinoleic, palmitic or stearic acids, copra oil acids or hydrogenated copra oil and in particular the amine salts, such as amine stearates.

The following can also be mentioned:

the acyl lactylates, the acyl radical of which contains 8 to 20 carbon atoms, the carboxylic acids of polyglycolic ethers corresponding to the formula:

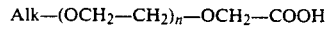

Alk—(OCH$_2$—CH$_2$)$_n$—OCH$_2$—COOH in the acid or salt form in which the Alk substituent corresponds to a linear chain having from 12 to 18 carbon atoms and where n is an integer of between 5 and 15.

Among the non-ionic tensio-active agents which can be used alone or in combination, the following in particular can be mentioned: alcohols, polyethoxylated, polypropoxylated or polyglycerolated alkylphenols and fatty acids with a fatty chain containing 8 to 18 carbon atoms. The following can also be mentioned: ethylene and propylene oxide copolymers, ethylene and propylene oxide condensates on fatty alcohols, polyethoxylated fatty amides, polyethoxylated fatty amines, ethanolamides, glycol fatty acid esters, oxyethylenated or non-oxyethylenated sorbitan fatty acid esters, saccharose fatty acid esters, polyethyleneglycol fatty acid esters, phosphoric triesters, fatty acid esters of glucose derivatives.

Other compounds in this class are the condensation products of an α-diol, a monoalcohol, an alkylphenol, an amide or a diglycolamide with glycidol or a glycidol precursor. In particular, these condensation are:

those of the formula:

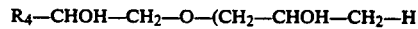

R$_4$—CHOH—CH$_2$—O—(CH$_2$—CHOH—CH$_2$—H wherein R$_4$ designates an aliphatic, cycloaliphatic or arylaliphatic radical preferably having between 7 and 21 carbon atoms and mixtures thereof, with the aliphatic chains capable of containing ether, thioether or hydroxymethylene groups, and where p is between 1 and 10 inclusive, such as described in French Patent 2,091,516;

those of the formula:

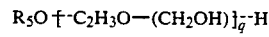

R$_5$O—(C$_2$H$_3$O—(CH$_2$OH)]$_q^-$-H wherein R$_5$ designates an alkyl, alkenyl or alkylaryl radical and q is a statistical value of between 1 and 10 inclusive, such as described in French Patent 1,477,048;

or those of the formula:

$R_6-CONH-CH_2-CH_2O-CH_2-CH_2-O-CH_2-CHOH-CH_2-O$ wherein $R_6$ designates a radical or a mixture of linear or branched, saturated or unsaturated aliphatic radicals which can possibly contain one or several hydroxyl group(s), having between 8 and 30 carbon atoms, of synthetic or natural origin, r represents an integer or decimal number from 1 to 5 an designates the degree of average condensation, such as are described in French Patent 2,328,763.

The non-ionic emulsions are principally composed of a mixture of oil an/or fatty alcohol, or polyethoxylated or polyglycerolated alcohols, such as polyethoxylated stearylic or cetylstearylic alcohols.

The anionic emulsions are preferably constituted from amine stearates.

In addition to the above-mentioned ingredients, the compositions in accordance with the present invention can contain ingredients which are conventionally used in particular in make-up compositions and which are selected from among softeners, preservatives, sequestoring agents, perfumes, thickeners, oils, silicones, cohesion agents and polymers as well as the alkalizing or acidifying agents normally used in the cosmetic field.

The thickeners which can be used can be natural or synthetic. Among the natural thickeners, gums of various sorts, such as gum Arabic, guar or carob gum can be mentioned. Among the synthetic thickeners, cellulose derivatives such as hydroxyethylcellulose, carboxymethylcellulose, starch derivatives, cellulose ether derivatives having quaternary ammonium groups, cationic polysaccharides, acrylic or methacrylic polymer salts, polyenes or polysiloxanes can be mentioned.

A thickener for the compositions can also be obtained with a mixture of polyethyleneglycol and polyethyleneglycol stearate and/or distearate or with a mixture of phosphoric esters and fatty amides.

The compositions in accordance with the invention also contain components which are generally considered as a cosmetically acceptable support, a solvent or a mixture of aqueous or anhydrous solvents.

The present invention also relates to a method of manufacture of a composition in accordance with the invention consisting of combining a cosmetically acceptable support with a wax having a melting point of between 60° and 110° C. and a keratin hydrolysate having an average molecular weight of between 50,000 and 200,000, with the ratio by weight of the quantity of keratin hydrolysate used to the quantity of wax(es) used being between 0.005 and 0.5.

A further object of the invention is a method for making up eyelashes using a composition such as defined above.

In order to better understand the object of the invention, by way of purely illustrative and non-limiting examples, several methods of use will be described below.

In the examples given below, a keratin hydrolysate was used, which is sold by CRODA CHEMICALS LTD. under the name "KERASOL", which has an average molecular weight of 100,000 and which has the following composition in % by weight:

| | |
|---|---|
| Isoleucine | 4.9 |
| Leucine | 10.6 |
| Lysine | 5.5 |
| Methionine | 1.5 |
| Cystine | 2.0 |
| Phenylalanine | 3.9 |
| Threonine | 4.8 |
| Tyrosine | 1.4 |
| Valine | 5.2 |
| Arginine | 7.6 |
| Histidine | 3.8 |
| Alanine | 4.2 |
| Aspartic acid | 9.1 |
| Glutamic acid | 11.4 |
| Glycine | 3.3 |
| Proline | 2.4 |
| Serine | 8.3 |

It was used in the form of a solution containing 14% protein hydrolysate, 15% propyleneglycol, 3% NaCl and 67% water, with a pH of 5-7.

EXAMPLE 1

The mascara composition with the following formula was prepared:

| | |
|---|---|
| Carnauba wax | 5 g |
| Candelilla wax | 5 g |
| Ethyl alcohol | 3 g |
| Montmorillonite modified with an organic substance | 4 g |
| Keratin hydrolysate (calculated by dry weight) | 0.3 g |
| Talc | 10 g |
| Black iron oxide | 10 g |
| Isoparaffin quantity sufficient for | 100 g |

The method was the following:
The waxes were heated to 80° C. The talc and the pigments were added. The montmorillonite which had been modified with an organic substance and part of the isoparaffin were then incorporated. At approximately 40° C., the keratin hydrolysate, the ethyl alcohol and the remainder of the isoparaffin were added. The mixture was passed through a grinder.

This mascara, with a very rapid application time, provided a good make-up by coating the eyelashes and increasing their length.

The following Examples 2 to 7 relate to mascara compositions in emulsion form. These mascaras are ready for use. The general method was the following:

The waxes were melted. The pigments were incorporated. The aqueous phase containing, depending on the case, the gums and/or the hydroxyethylcellulose and the keratin hydrolysate were heated to the same temperature as the wax phase. The two phases were mixed and vigorously stirred.

The mascaras obtained in this manner, the formulations of which are given below, require relatively short application times but, however, provide good make-ups.

EXAMPLE 2

The mascara composition with the following formula was prepared:

| | |
|---|---|
| Triethanolamine stearate | 15 g |
| Beeswax | 8 g |
| Paraffin | 3 g |
| Colophony | 2 g |
| Ozocerite | 10 g |
| Propyl parahydroxybenzoate | 0.20 g |
| Methyl parahydroxybenzoate | 0.20 g |
| Gum Arabic | 0.50 g |
| Keratin hydrolysate (calculated by dry weight) | 0.15 g |

-continued

| | |
|---|---|
| Black iron oxide | 5 g |
| Aluminosilicate polysulfide | 5 g |
| Water quantity sufficient for | 100 g |

EXAMPLE 3

The mascara composition with the following formula was prepared:

| | |
|---|---|
| 2-amino 2-methyl 1-propanol stearate | 25 g |
| Candelilla wax | 5 g |
| Beeswax | 8 g |
| Methyl parahydroxybenzoate | 0.15 g |
| Propyl parahydroxybenzoate | 0.15 g |
| Carob gum | 3 g |
| Xanthan gum | 3 g |
| Keratin hydrolysate (calculated by dry weight) | 0.08 g |
| Black iron oxide | 8 g |
| Water quantity sufficient for | 100 g |

EXAMPLE 4

The mascara composition with the following formula was prepared:

| | |
|---|---|
| Triethanolamine stearate | 20 g |
| Microcrystalline wax | 5 g |
| Carnauba wax | 10 g |
| Beeswax | 3 g |
| Urea imidazolidinyl | 0.30 g |
| Propyl parahydroxybenzoate | 0.15 g |
| Tragacanth gum | 5 g |
| Keratin hydrolysate (calculated by dry weight) | 0.60 g |
| Black iron oxide | 5 g |
| Water quantity sufficient for | 100 g |

EXAMPLE 5

The mascara composition with the following formula was prepared:

| | |
|---|---|
| Triethanolamine stearate | 15 g |
| Candelilla wax | 8 g |
| Carnauba wax | 10 g |
| Hydroxyethylcellulose | 0.9 g |
| Keratin hydrolysate (calculated by dry weight) | 0.75 g |
| Black iron oxide | 8 g |
| Methyl parahydroxybenzoate | 0.15 g |
| Propyl parahydroxybenzoate | 0.15 g |
| Water quantity sufficient for | 100 g |

EXAMPLE 6

The mascara composition with the following formula was prepared:

| | |
|---|---|
| Triethanolamine stearate | 10 g |
| Candelilla wax | 15 g |
| Beeswax | 17 g |
| Xanthan gum | 1 g |
| Keratin hydrolysate (calculated by dry weight) | 0.15 g |
| Black iron oxide | 5 g |
| Aluminosilicate polysulfide (ultramarine blue) | 4 g |
| Preservative | sufficient quantity |
| Water quantity sufficient for | 100 g |

EXAMPLE 7

The mascara composition with the following formula was prepared:

| | |
|---|---|
| Triethanolamine stearate | 10 g |
| Carnauba wax | 8 g |
| Beeswax | 8 g |
| Keratin hydrolysate (calculated by dry weight) | 1 g |
| Black iron oxide | 5 g |
| Aluminosilicate polysulfide | 4 g |
| Preservative | sufficient quantity |
| Water quantity sufficient for | 100 g |

EXAMPLE 8

An anhydrous block of mascara with the following formula was prepared:

| | |
|---|---|
| Triethanolamine stearate | 25 g |
| Beeswax | 6 g |
| Microcrystalline wax | 22 g |
| Saturated fatty acid glycerides | 11 g |
| Methyl parahydroxybenzoate | 0.15 g |
| Propyl parahydroxybenzoate | 0.15 g |
| Gum Arabic | 5.70 g |
| Keratin hydrolysate (calculated by dry weight) | 0.25 g |
| Red iron oxide | 5 g |
| Black iron oxide | 5 g |

The method was the following:
The waxes were melted. The pigments were added. The gum Arabic and the keratin hydrolysate were incorporated. The mixture was passed through a heating grinder. The remaining ingredients were added. The entire mixture was again melted and poured into molds while stirring lightly.

Good eyelash make-up was obtained in a very short application time.

We claim:

1. An eyelash makeup composition comprising in a cosmetically acceptable support at least one wax having a melting point between 60° and 110° C. and at least one keratin hydrolyzate having an average molecular weight ranging from 50,000 to 200,000, the weight ratio of the amount of said keratin hydrolyzate to the amount of said wax ranging from 0.005 to 0.5.

2. The composition of claim 1 wherein said keratin hydrolyzate has a molecular weight of approximately 100,000.

3. The composition of claim 1 wherein said keratin hydrolyzate is derived from hair, wool, hooves, horn, fur, silk or feathers.

4. The composition of claim 1 wherein said wax is an animal wax, a vegetable wax, a mineral wax, a synthetic wax or fraction of a natural wax, or a mixture thereof.

5. The composition of claim 4 wherein said animal wax is selected from the group consisting of beeswax, lanolin wax and China insect wax.

6. The composition of claim 4 wherein said vegetable wax is selected from the group consisting of Carnauba wax, Candelilla wax, Ouricurry wax, cork fiber wax, sugar cane wax and Japan wax.

7. The composition of claim 4 wherein said mineral wax is selected from the group consisting of paraffin, microcrystalline wax, Montan wax and ozokerite.

8. The composition of claim 4 wherein said synthetic wax is selected from the group consisting of polyethylene wax, wax obtained by Fischer-Tropsch synthesis and a wax copolymer and esters thereof.

9. The composition of claim 1 wherein said wax is present in an amount ranging from 2 to 40 percent by weight based on the total weight of said composition.

10. The composition of claim 1 wherein said keratin hydrolyzate is present in an amount ranging from 0.05 to 5 percent by weight based on the total weight of said composition.

11. The composition of claim 1 which also includes at least one mineral, organic or pearly pigment.

12. The composition of claim 11 wherein said mineral pigment is selected from the group consisting of titanium dioxide, surface treated titanium dioxide, black iron oxide, yellow iron oxide, red iron oxide, brown iron oxide, manganese violet, ultramarine blue, chromium oxide, chromium hydrate and ferric blue.

13. The composition of claim 11 wherein said organic pigment is selected from the group consisting of D&C red No. 19, D&C red No. 9, D&C red No. 21, D&C orange No. 4, D&C orange No. 5, D&C red No. 27, D&C red No. 13, D&C red No. 7, D&C red No. 6, D&C yellow No. 5, D&C red No. 36, D&C orange No. 10, D&C yellow No. 6, D&C red No. 30, D&C red No. 3 and cochineal carmine based lacquer.

14. The composition of claim 11 wherein said pearly pigment is selected from the group consisting of mica covered with titanium oxide, bismuth oxychloride, titanium mica colored with an iron oxide, titanium mica colored with ferric blue, chromium oxide, titanium mica colored with an organic pigment and colored bismuth oxychloride.

15. The composition of claim 11 wherein said pigment is present in an amount ranging from 3 to 20 percent by weight based on the total weight of said composition.

16. The composition of claim 1 in the form of an oil-in-water emulsion, a water-in-oil emulsion, a suspension in a solvent medium, an anhydrous solid or an anhydrous paste.

17. The composition of claim 1 which also includes at least one tensio-active agent present in an amount ranging from 2 to 30 percent by weight based on the total weight of said composition.

18. The composition of claim 1 which also includes at least one of a softener, a preservative, a sequestering agent, a perfume, a thickener, an oil, a silicone, a cohesion agent, a polymer, an alkalizing agent or an acidifying agent.

19. A method for preparing the composition of claim 1 comprising combining a cosmetically acceptable support with a wax having a melting point ranging from 60° to 110° C. and a keratin hydrolyzate having an average molecular weight ranging from 50,000 to 200,000, the weight ratio of the amount of said keratin hydrolyzate to the amount of said wax ranging from 0.005 to 5.

* * * * *